United States Patent [19]

Stutts

[11] 4,166,220
[45] Aug. 28, 1979

[54] ADD-ON COLLIMATOR CAP FOR DENTAL X-RAY COLLIMATOR TUBE AND DENTAL X-RAY SYSTEM THEREWITH

[76] Inventor: William F. Stutts, 7017 Briar Cove Dr., Dallas, Tex. 75240

[21] Appl. No.: 790,876

[22] Filed: Apr. 26, 1977

[51] Int. Cl.² .............................................. G21K 1/00
[52] U.S. Cl. .................................. 250/505; 250/479; 250/482
[58] Field of Search .................... 250/505, 479, 482

[56] References Cited

U.S. PATENT DOCUMENTS

| | | | |
|---|---|---|---|
| 3,102,957 | 9/1963 | Slauson | 250/505 |
| 3,745,344 | 7/1973 | Updegrave | 250/479 |
| 3,864,576 | 2/1975 | Stevenson | 250/505 |
| 4,109,156 | 8/1978 | Schroeder | 250/505 |

*Primary Examiner*—Alfred E. Smith
*Assistant Examiner*—T. N. Grigsby

*Attorney, Agent, or Firm*—Watson, Cole, Grindle & Watson

[57] ABSTRACT

A collimator cap for insertion over the output end of a dental x-ray machine collimator tube comprises a housing composed of a hollow longitudinal portion and a radially inwardly extending flanged portion at one end thereof forming an opening therethrough, a removable lead diaphragm positioned within the hollow longitudinal portion of the housing and adjacent the flanged portion, the lead diaphragm including an aperture therethrough of predetermined size and shape, and a shim for fixing the lead diaphragm in place. The end of the hollow longitudinal portion of the housing opposite the flanged portion is insertable over the output end of an x-ray machine collimator tube. In conjunction with use of the collimator add-on cap, a film cassette and cassette holder is used in order to take four exposures on one film, based on the x-ray beam size and shape eminating through the lead diaphragm aperture.

16 Claims, 8 Drawing Figures

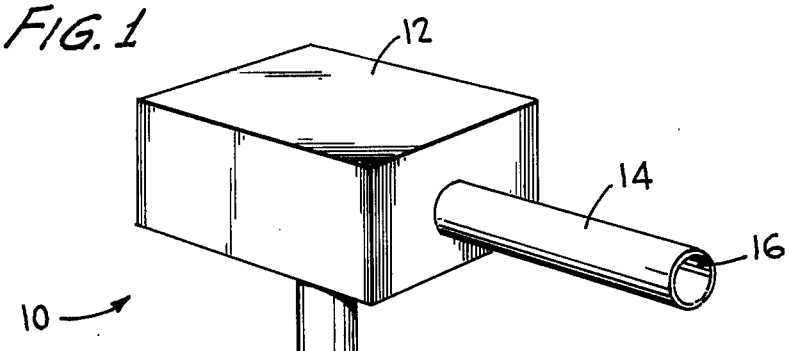
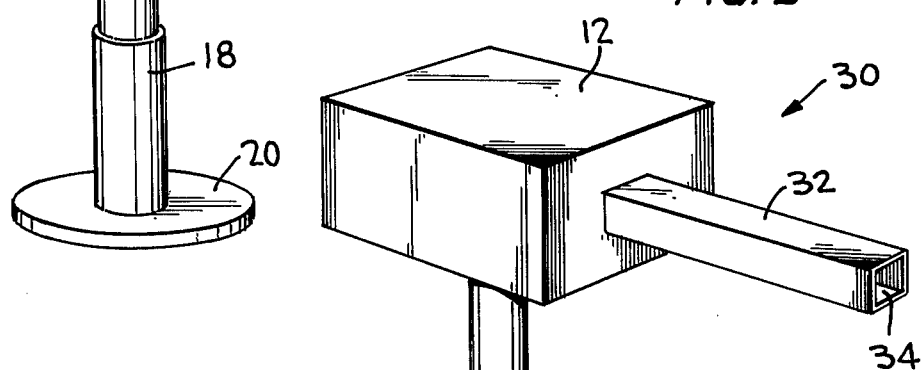
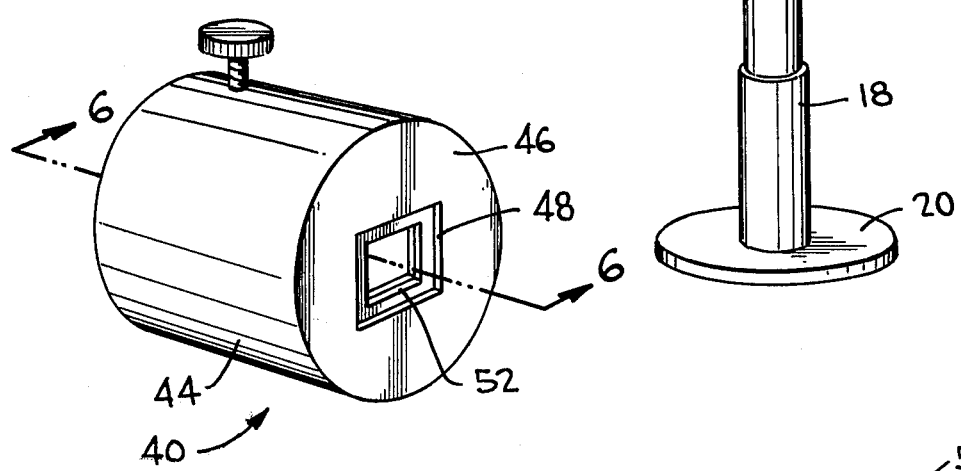
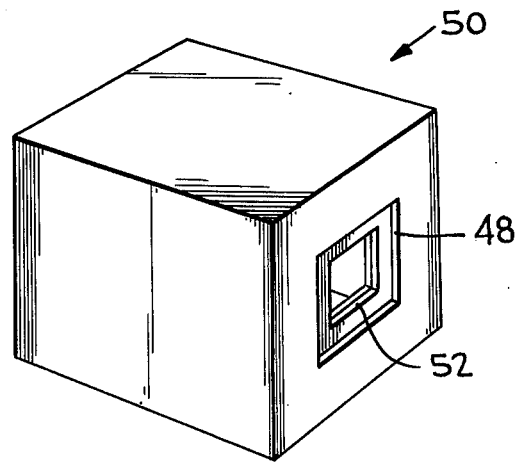

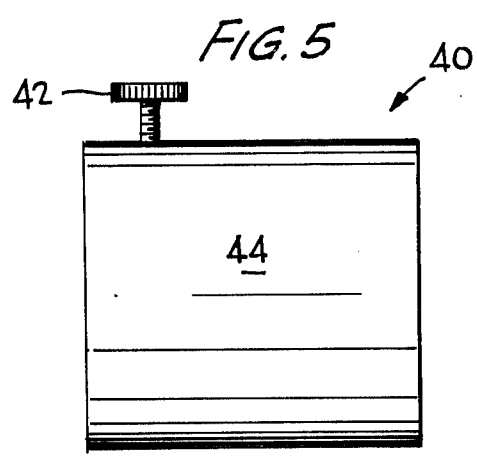
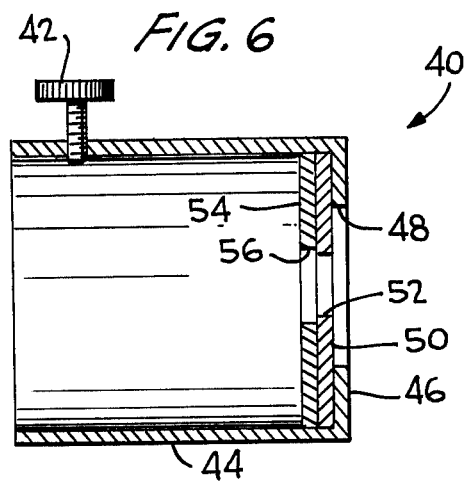
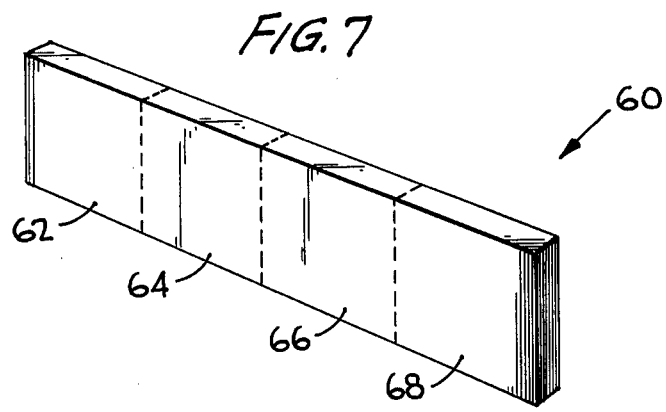
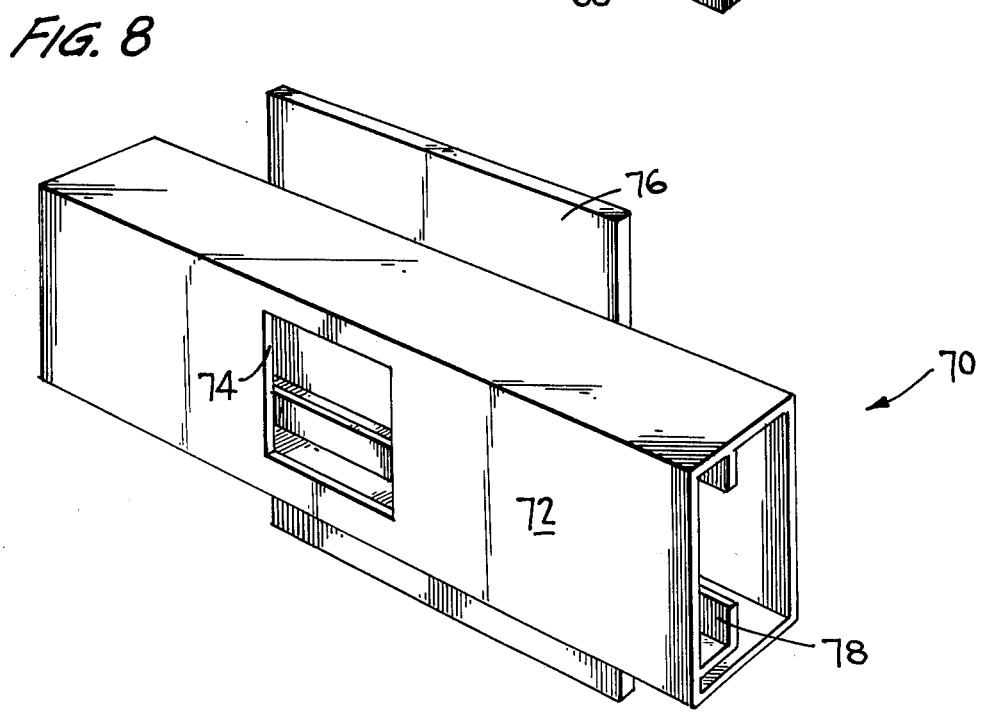

ADD-ON COLLIMATOR CAP FOR DENTAL X-RAY COLLIMATOR TUBE AND DENTAL X-RAY SYSTEM THEREWITH

BACKGROUND OF THE INVENTION

Physicians and dentists throughout the United States and indeed throughout the world utilize x-ray machines in the course of their medical practice. Such x-ray machines allow such practitioners to obtain pictures of their patient's bodies in order to help diagnose possible diseases, malformities, etc. In the case of dentistry, the dentist, orthodontist or oral surgeon can obtain pictures of a patient's head bones, such as their jaw bones, cheek bones, etc., as well as obtain pictures of a patient's teeth, in order to discover the location and orientation of impacted teeth, concealed cavities, jaw fractures, pathology, etc.

In the past it has been customary, when for example taking x-ray pictures of a patient's teeth, for the unexposed film to be inserted within the patient's mouth (intra-oral exposure) and for the x-ray machine collimator tube to be appropriately positioned so as to obtain an exposure of the desired teeth. Such procedures are many times uncomfortable for the patients because of the gagging reflex when the film is inserted deep within the mouth, and in addition, such procedures generally require many repositionings of the x-ray machine itself if multiple views of a patient's mouth and teeth are needed.

In the past it has also been customary to utilize much larger cross-section beams of x-rays when taking pictures of, for example, a patient's mouth than the size of the film to be exposed, whether or not the film is placed inside or outside the patient's mouth, and this is true even though collimator tubes has been employed to reduce generally the size of the beam to some extent. This is because in the past the possible harmful side effects of exposure to x-rays have not fully appreciated.

Recently it has become well recognized that exposure to x-rays is detrimental to human beings and has been associated with an increase in cancerous cell development. As a result, the United States Department of Health, Education and Welfare has recently issued rules requiring that x-ray beams, when used in medical diagnosis, be sufficiently collimated such that the beam size and shape exceed the size of the film by no more than two precent, regardless of the distance which may be required or desired between the x-ray machine and the film. Of course, the film utilized is also expected to be no larger than what would be reasonably necessary to obtain a picture of the area which is under medical investigation.

X-ray machines which include lead or lead-lined collimator tubes are expensive to make and replace, and thus to provide for the required collimation of an x-ray beam eminating from an x-ray machine already in medical use in a fairly inexpensive and easy fashion is desired.

According to U.S. Pat. No. 2,939,008 to Goodfriend, it has already been proposed to collimate an x-ray beam eminating from a lead-lined collimator tube of a dental x-ray machine by using a removable lead apertured diaphragm positioned at the end of the collimator tube adjacent the patient's head (the film to be exposed being outside the patient's mouth). In addition, it is noted therein that the usefulness of such a diaphragm is to reduce the size of the collimated x-ray beam in order to minimize the exposure of the patient to x-rays, while at the same time obtaining the desired radiograph of the patient's body, such as his head (e.g., temporomandibular joint). However, the mentioned "removable lead apertured diaphragm" is not described as to its specific structural features or its operation; thus, the Goodfriend disclosure is actually non-enabling in this regard in teaching those in the art how such a diaphragm would be constructed, how it might operate, how it might perhaps be removably attached to the collimator tube, etc.

Thus, it is an object of the present invention to provide a collimator cap which can be easily inserted over the output end of a collimator tube of an x-ray machine, e.g., a dental x-ray machine, in order to confine the beam of x-rays to a predetermined size and shape, and which can be easily removed and replaced.

Furthermore, it is an object of the present invention to provide a collimator cap which can be constructed of an inexpensive material, which need not necessarily be entirely impervious to x-rays, which can be fitted with replaceable diaphragms which are made of x-ray impervious materials such as lead, which have the appropriately sized and shaped apertures therein.

Furthermore, it is an object of the present invention to provide a collimator cap which is inexpensive to produce, which can be produced in varying sizes and shapes in order to fit the output ends of any collimator tubes on existing x-ray machines, and which can contain lead diaphragms in the form of apertured lead plates that are easily replaceable so that for any given distance between diaphragm and film and for any shape of film to be exposed, the x-ray beam will not be any larger than 2% of the dimensions of the film zone to be exposed.

In addition, it is an object of the present invention to provide an x-ray system, such as a dental x-ray system, which will employ the collimator cap of the present invention, and which will concurrently employ a film cassette and film cassette holder which will allow for four separate exposures to be made on the same film.

Further features of the present invention will be apparent in the arrangement and construction of the constituent parts in detail as set forth in the following specification taken together with the accompanying drawings.

SUMMARY OF THE PRESENT INVENTION

According to the present invention, an add-on collimator cap is provided for insertion over the output end of a dental x-ray machine collimator tube, the cap acting to confine the beam of x-rays to a predetermined size and shape. The add-on collimator cap is comprised of a housing which includes a hollow longitudinal portion and a radially inwardly extending flanged portion at one end thereof, the flanged portion forming a generally centrally located opening therethrough for general alignment with a beam of x-rays eminating from the dental x-ray machine through the collimator tube. The cap also includes a lead diaphragm which is removably positioned within the hollow longitudinal portion of the housing and adjacent to the flanged portion thereof, this diaphragm having a generally centrally located opening therethrough of a predetermined size and shape to confine the x-ray beam to the predetermined size and shape, the diaphragm being readily exchangeable in the housing so that the opening therethrough can be selected to confine the beam dimensions to predetermined levels. The cap also includes a means positioned within the hollow longitudinal portion of the housing and adjacent to the lead diaphragm to fix the removable lead diaphragm in juxtaposition to the flanged portion of the housing, this means having an opening therethrough in registry with the opening in the diaphragm and at least as large in size as the opening in the diaphragm.

According to the present invention the hollow longitudinal portion of the housing is of sufficient size and shape to allow for the end thereof opposite to the end having the flanged portion to be inserted over the output end of an existing dental x-ray machine collimator tube. The housing may also include a means for fixedly attaching itself to the output end of the collimator tube once insert thereover.

DESCRIPTION OF THE DRAWINGS

In the drawings,

FIG. 1 shows an isometric view of a conventional dental x-ray machine which includes a collimator tube having a circular cross-section;

FIG. 2 shows an isometric view of a second type of conventional dental x-ray machine which includes a collimator tube having a rectangular cross-section;

FIG. 3 shows an isometric view of a collimator cap according to the present invention which would be operable on a conventional x-ray machine as shown in FIG. 1;

FIG. 4 shows an isometric view of a collimator cap according to the present invention which would be operable on a conventional x-ray machine as shown in FIG. 2;

FIG. 5 shows a side view of the collimator cap shown in FIG. 3;

FIG. 6 is a sectional view along line 6—6 of FIG. 3;

FIG. 7 is an isometric view of a film cassette for use in taking x-ray pictures in the x-ray system using the collimator cap of the present invention; and, FIG. 8 is an isometric view of a film cassette holder for containing the film cassette of FIG. 7.

DETAILED DESCRIPTION OF THE PREFERRED EMBODIMENTS

Referring to FIG. 1, there is shown a conventional x-ray machine, generally indicated by 10, which includes a head 12, a support column 18, a flat base 20, and which further includes a collimator tube 14 having an output end as indicated at 16. As can be clearly seen, the collimator tube has a circular cross-section, thereby resulting in the collimator tube having a cylindrical configuration. Such a collimator tube is shown, for example, in U.S. Pat. No. 3,864,576 to Stevenson. FIG. 2 shows a second type of conventional x-ray machine 30 (to which the present invention also is applicable) which has a collimator tube 32 with a rectangular cross-section, such that the output end thereof 34 also has a rectangular cross-section. Such a collimator tube is shown, for example, in U.S. Pat. No. 3,745,344 to Updegrave. Typical collimator tubes of the foregoing type have a length of from 4 to about 16 inches. The x-ray machines of FIGS. 1 and 2 are shown for reference purposes only, and the specific structural features shown in themselves form no part of the present invention.

Turning now to the add-on collimator cap of the present invention, FIG. 3 shows such a cap which would be useful on the collimator tube of an x-ray machine, for example, as depicted in FIG. 1. As can be seen, the cap, generally indicated by 40, has a circular cross-section and comprises a housing portion 44, a flanged portion 46 which includes an aperture formed therein identified as 48, and a means 42 in the form of a set screw for fixedly attaching the housing to the collimator tube once inserted over the output end thereof. The set screw of course is threaded and is fitted through a threaded hole in the housing 44.

FIG. 4 depicts an add-on collimator cap which is rectangular in cross-section so as to be useful for insertion over the output end of a collimator tube as shown in FIG. 2, and which, in this case, may utilize an internal indent (not shown) for engagement, alignment and keying on the collimator tube.

FIG. 5 shows the collimator cap 40 in its side view, whereas FIG. 6 shows a sectional view through section 6—6 of FIG. 3. As can be seen, within the housing portion 44 is positioned a lead diaphragm 50 which is adjacent to the flanged portion 46 of the cap, the lead diaphragm having a generally centrally located aperture 52 therethrough of a predetermined size and shape to appropriately confine the x-ray beam passing therethrough. The lead diaphragm 50 may in fact be in the form of an apertured lead plate. A means 54, which may be called a shim, is also positioned within the hollow longitudinal portion 44 adjacent to the lead diaphragm 50 which functions to fix the lead diaphragm in place adjacent to flanged portion 46. The means 54 has an opening therethrough 56 which is in registry with the aperture 52 in the lead diaphragm, and which is at least as large in size as the opening 52 in order that no interference with the x-rays which are intended to pass through opening 52 will result therefrom. The set screw 42 (and the opening in the housing portion 44 through which the set screw passes) is positioned as shown in FIG. 6, such that no interference thereon will result from the positioning of the lead diaphragm 50 and the means 54. Indeed, the set screw and opening therefor is positioned near the end of the housing portion which is to be inserted over the output end of the collimator tube.

Of course, the lead diaphragm 50 and means 54 may be disc-shaped or rectangular in shape depending upon the corresponding shape of housing portion 44.

FIG. 7 shows a film cassette, generally indicated by 60, which contains the film which is to be exposed to the x-rays eminating from a standard dental x-ray machine (as shown in FIGS. 1 or 2) when further collimated in size and shape by means of an add-on collimator cap (as shown in FIGS. 3 or 4). The film cassette is positioned so as to be outside the patient's mouth, but on the opposite side thereof to the x-ray machine. The film is divided by the depicted markings into four separate zones indicated by 62, 64, 66 and 68 such that each zone can be separately exposed to x-rays by appropriate positioning within a cassette carrier (see FIG. 8). The cassette carrier, generally indicated by 70, which is positionable by means 76 on a suitable support apparatus (not shown), comprises an open-ended rectangular box means 72 which is composed of a material which is impervious to the passage therethrough of x-rays, the box means being provided with a rectangular opening 74 through which the x-rays pass. A support structure 78 which extends the length of the box means, functions to support a film cassette (as in FIG. 7) for slidable passage past the opening 74. The opening 74 is constructed so as to be the same size and shape as zones 62, 64, 66 and 68 of the film to be exposed on cassette 60.

The operation of the dental x-ray system wherein the x-rays are emitted from the collimator tube of a conventional x-ray machine is as follows. First, the patient to be examined is situated on a chair and the patient's head is positioned at the appropriate level and orientation between the output end of an x-ray machine collimator tube and a support apparatus for an x-ray film cassette carrier. Then a film cassette carrier constructed as previously discussed is positioned on the support apparatus, the particular film cassette carrier being selected with respect to the opening 74 therein for obtaining the desired picture size. Thereafter, a film cassette of suitable size is inserted into the cassette carrier and positioned such that the opening in the cassette carrier will allow for an exposure of the first quadrant of the film cassette (such as zone 62 as shown in FIG. 7).

Subsequent to these steps, and based on the exact distance between the surface of the film cassette and the output end of the collimator tube, a suitable lead diaphragm is selected (from among a series of such diaphragms) which has an appropriately sized and shaped aperture therethrough so that the beam of x-rays emitted from the output end of the collimator tube will coincide almost exactly with the size and shape of the opening in the cassette carrier (and thus zone 62 on the film cassette 60). The suitable lead diaphragm is then inserted within the housing portion of the collimator cap and a positioning means is positioned adjacent to the lead diaphragm in order to fix the lead diaphragm in juxtaposition to the flanged portion of the housing. The collimator cap is then positioned or inserted over the output end of the collimator tube and secured thereon, for example by adjustment of a set screw to produce a frictional engagement. The sequence of four pictures can then be serially made on the film contained in the film cassette by appropriately moving the film cassette horizontally along the support structure within the film cassette holder.

Use of the inventive collimator cap with removable lead diaphragms is useful for collimating x-ray beams to any desired size and shape, and is much more inexpensive than replacing entire x-ray machines and/or collimator tubes in order to comply with the recent requirements regarding the limiting of x-ray beam dimensions in relationship to the film to be exposed.

I claim:

1. An add-on collimator cap for insertion over the output end of a collimator tube of a dental x-ray machine to confine the beam of x-rays to a predetermined size and shape, said add-on collimator cap comprising:
   a housing which includes a hollow longitudinal portion and a radially inwardly extending flanged portion at one end thereof, said flanged portion forming a generally centrally located opening therethrough for general alignment with a beam of x-rays eminating from the dental x-ray machine through the collimator tube,
   a lead diaphragm removably positioned within said hollow longitudinal portion of said housing and adjacent to said flanged portion thereof, said diaphragm having a generally centrally located aperture therethrough of a predetermined size and shape to confine the x-ray beam to the predetermined size and shape, said diaphragm being readily exchangable in said housing so that the aperture therethrough can be selected to confine the beam dimensions to predetermined levels,
   means positioned within said hollow longitudinal portion of said housing and adjacent to said lead diaphragm to fix said removable lead diagram in juxtaposition to said flanged portion of said housing, said means having an opening therethrough in registry with the aperture in said diaphragm and at least as large in size as said aperture in said diaphragm, and
   said hollow longitudinal portion of said housing being of sufficient size and shape for insertion of a second end thereof over the output end of a dental x-ray machine collimator tube.

2. An add-on collimator cap as defined in claim 1 including a means for fixedly attaching said housing to the output end of a dental x-ray machine collimator tube.

3. An add-on collimator cap as defined in claim 2 wherein said means for fixedly attaching said housing to the output end of a dental x-ray machine collimator tube comprises a set screw, said set screw being threaded in a threaded hole in said hollow longitudinal portion of said housing near the second end thereof so as to be adjustably positionable.

4. An add-on collimator cap as defined in claim 1 wherein said hollow longitudinal portion of said housing is rectangular in cross-section.

5. An add-on collimator cap as defined in claim 4 wherein said lead diaphragm is rectangular in shape.

6. An add-on collimator cap as defined in claim 4 wherein said means positioned within said hollow longitudinal portion of said housing to fix said removable lead diaphragm in juxtaposition to said flanged portion of said housing comprises a rectangular shaped shim.

7. An add-on collimator cap as defined in claim 1 wherein said hollow longitudinal portion of said housing is circular in cross-section.

8. An add-on collimator cap as defined in claim 7 wherein said lead diaphragm is disc shaped.

9. An add-on collimator cap as defined in claim 8 wherein said means positioned within said hollow longitudinal portion of said housing to fix said removable lead diaphragm in juxtaposition to said flanged portion of said housing is a disc shaped shim.

10. An add-on collimator cap as defined in claim 1 wherein said housing is composed of aluminum.

11. An add-on collimator cap as defined in claim 1 wherein said means positioned to fix said removable lead diaphragm in juxtaposition to said flanged portion of said housing is composed of aluminum.

12. An x-ray device which limits the beam of x-rays emitted therefrom to a predetermined size and shape which comprises an x-ray generating head portion; a collimator tube connected to said head portion for conveying x-rays away from said head portion, said collimator tube having an end portion remote from said head portion, and an add-on collimator cap as defined in claim 1 attached to said end portion of said collimator tube.

13. An x-ray device according to claim 12 wherein said collimator tube is rectangular in cross-section and wherein said hollow longitudinal portion of said housing is rectangular in cross-section.

14. An x-ray device according to claim 12 wherein said collimator tube is circular in cross-section and wherein said hollow longitudinal portion of said housing is circular in cross-section.

15. In combination, an x-ray machine which emits a beam of x-rays having a predetermined size and shape which comprises an x-ray generating head portion, a collimator tube connected to said head portion for conveying x-rays away from said head portion, said collimator tube having an end portion remote from said head portion, and an add-on collimator cap as defined in claim 1 attached to said end portion of said collimator tube; a rectangular film-containing cassette placed in the path of the x-rays emitted by said x-ray machine; said film-containing cassette being placed within a cassette carrier which comprises a rectangular box-shaped housing having open longitudinal sides, said box-shaped housing having a rectangular cut-out portion on the side thereof facing said x-rays, said cut-out portion being of a corresponding shape with the x-rays emitted by said x-ray machine and a register therewith and of such a size that the size of the beam of x-rays exactly corresponds with the size of the cut-out portion when said beam passes therethrough to expose said film contained therein.

16. The combination as defined in claim 15 wherein the size of said rectangular cut-out portion of said rectangular box-shaped housing is one fourth the size of the film contained therein, such that said film, upon appropriate movement of said cassette placed within said cassette carrier, can have four separate exposures formed thereon.

* * * * *